United States Patent [19]

Kolln

[11] Patent Number: 4,722,734
[45] Date of Patent: Feb. 2, 1988

[54] DEVICE FOR THE INTERMITTENT PULSATORY APPLICATION OF LIQUID PHARMACEUTICALS

[75] Inventor: Harm Kolln, Kiel, Fed. Rep. of Germany

[73] Assignee: Ferring Biotechnik, GmbH, Fed. Rep. of Germany

[21] Appl. No.: 888,266

[22] Filed: Jul. 18, 1986

Related U.S. Application Data

[63] Continuation of Ser. No. 633,985, Jul. 25, 1984, abandoned.

[30] Foreign Application Priority Data

Apr. 14, 1984 [EP] European Pat. Off. ........ 84104242.7

[51] Int. Cl.⁴ .............................................. A61M 1/00
[52] U.S. Cl. ...................................... 604/151; 604/67; 604/246; 128/DIG. 12
[58] Field of Search ................... 604/67, 131, 151–155, 604/246, 29; 128/DIG. 12, DIG. 13

[56] References Cited

U.S. PATENT DOCUMENTS

| | | | |
|---|---|---|---|
| 4,077,405 | 3/1978 | Haertan et al. | 128/DIG. 13 |
| 4,308,866 | 1/1982 | Jelliffe et al. | 604/67 |
| 4,397,639 | 8/1983 | Eschweiler et al. | 604/153 |
| 4,469,481 | 9/1984 | Kobayashi | 604/151 |
| 4,475,901 | 10/1984 | Kraegen et al. | 604/67 |
| 4,498,843 | 2/1985 | Schneider et al. | 604/67 |
| 4,559,037 | 12/1985 | Franetzki et al. | 604/151 |

FOREIGN PATENT DOCUMENTS

| | | |
|---|---|---|
| 0039044 | 4/1981 | European Pat. Off. . |
| 3307810 | 7/1983 | Fed. Rep. of Germany . |
| 2387046 | 6/1978 | France . |
| 2384134 | 10/1978 | France . |
| 610763 | 1/1980 | Switzerland . |

*Primary Examiner*—C. Fred Rosenbaum
*Assistant Examiner*—Mario Costantino
*Attorney, Agent, or Firm*—Pearne, Gordon, McCoy & Granger

[57] ABSTRACT

A device for the intermediate pulsatory application of liquid pharmaceuticals or medicine is provided which has a changeable storage container for the pharmaceutical connected to one end of a flexible tube; on the other end of the tube are a catheter, a rolling pump which works on the tube, a drive motor for the rolling pump, and a timer for delivery impulse and pause time of the rolling pump. To control the operation of the drive motor, there is a microcomputer with program storage. The microcomputer is programmable by means of a keyboard. Proper program operation is always guaranteed, including when interruptions in the drive appear necessary, for example, to renew the battery serving as the energy source.

10 Claims, 4 Drawing Figures

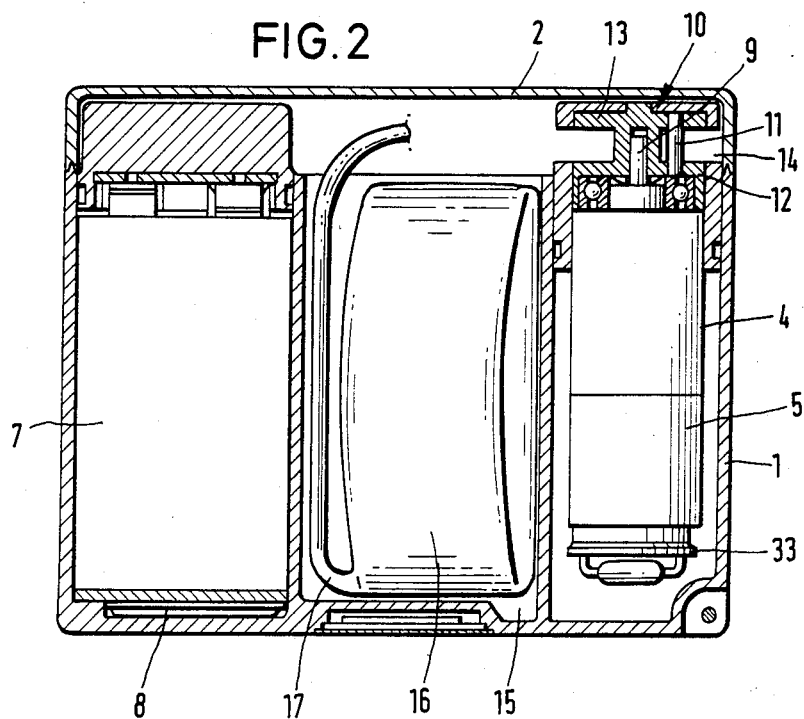
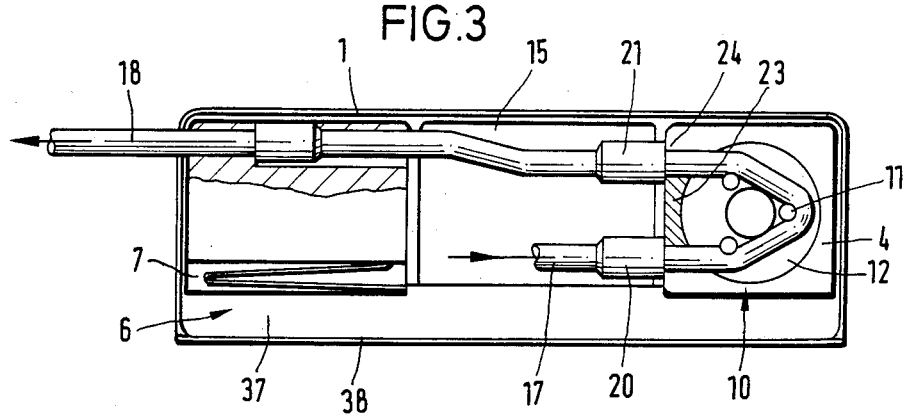

DEVICE FOR THE INTERMITTENT PULSATORY APPLICATION OF LIQUID PHARMACEUTICALS

This is a continuation of application Ser. No. 633,985, filed on July 25, 1984, now abandoned.

BACKGROUND OF THE INVENTION

The invention concerns a device for the intermittent pulsatory application of liquid pharmaceuticals or medicine. The device has an interchangeable storage container for the medicine and a connecting flexible tube that can be joined on the outside end to a catheter. A roller or rolling pump operated by a drive motor cooperates with the tube. A timer is provided for the delivery impulse and resting times of the rolling pump.

The operational control for a known device of this sort (EP-OSO No. 039 044 A 1) is still inadequate. In fact, a simple computer program provided with a timing element having a timing generator, a frequency divider, and a driving stage to measure a resting period and application period could be employed. However, the adjustment of the program would be troublesome and in the end too uncertain. Additionally, problems in running the program, for example, when a tube collapses or becomes clogged, or a drive transistor burns out, can go unnoticed. This presents the risk that the device will deliver too small or great a dose of the medicine.

SUMMARY OF THE INVENTION

The invention has the object to improve the sort of apparatus known from EP-OSO No. 039 044 A 1: that the device can be easily and securely adjusted according to the requirements of each patient, have the ability to avoid problems in the program operation, and have the ability when problems might occasionally occur to determine that immediately and, then easily and without further complication, eliminate them.

The object set forth above is solved in accordance with the invention by providing a keyboard programmable microcomputer having program storage to control the drive motor and, accordingly, the rolling pump. In addition, the microcomputer can have a clock with a calendar attached to it.

With this device, the user, in particular the doctor, can specify a program of treatment or agenda specially determined for each patient, and can also store these programs for long periods of treatment. The programs can be created in the hospital, nursing home, or patient's home, since the possible program steps can be arbitrarily divided or grouped. Therefore, it is not necessary to program the microcomputer with only a fixed cycle plan or program, but it is possible to combine in operation several of the stored program steps or groups thereof in a variety of selections between several applications within a operation sequence specifically designed for the treatment of the individual.

In a further feature of the invention, the microcomputer can include a speed indicator for the drive motor. Thus, the speed of the motor, and thereby the rolling pump, can be supervised, so that mistakes in the operation of the program can be immediately determined and remedied.

As a further feature of the invention, the device is provided with a display by which the entered data can be supervised and which can also be used to more exactly point out the disturbance to which the observer is alerted, such as when the motor runs incorrectly, the medicinal reservoir is exhausted, and the like. In addition, the microcomputer can be connected to a signal generator, for example, an acoustic signal generator, to indicate a disturbance or defect. The disturbance, or respectively the defect, can be determined by the sounding of the signal tone of the generator so that help can be immediately forthcoming.

A further additional feature of the invention is that electric safety means switch off the drive motor of the rolling pump in the event that an element of the microcomputer system is defective, for example, the clock, the calendar indicator, or the microcomputer itself. Correspondingly, the rolling pump is kept from uncontrolled operation.

In accordance with a further feature of the invention, a 9-volt drive battery is provided as the main energy source. In addition, a 3-volt button cell battery is available to safeguard the memory-stored data during a drive battery change, or when the drive battery wears out. The button cell has a relatively long life, since it is rarely used.

The keyboard is coordinated with several program data fields so that each program routine can be individually adjusted with respect to its operation. One program data field serves, for example, to adjust the pause time, and a further program field to adjust the time of delivery. Each control function of the microcomputer is adjusted correspondingly by its own program field. Details of the programming are further explained below.

Since the device has an audible signal to indicate disturbances or breakdowns in the operation of the program, the device can be used with greater operational safety or security. Thus, if the motor operates contrary to the program, the audible signal will immediately indicate the problem exists, for example, if the motor runs slowly or stops because the tube is clogged, or if the motor runs too fast and delivers too much medicine because a drive transistor burns out.

Furthermore, the acoustic signal can also be used in order to indicate when a previously determined volume of medicine is needed. To this end, the microcomputer or microprocessor calculates the amount of liquid needed during the single delivery period. One can call up this data at any time and, by means of the indicator, can be assured that the necessary amount of medicine remains in the storage container, even before the signal indicates that the medicine storage will soon be exhausted. Thus, the acoustic signal sounds an alarm when the storage container is not yet exhausted of medicine so that the user can exchange the used storage container before it is exhausted.

The type of programming is therefore particularly important because the user, for example, the doctor, can work with single data fields. Therefore, he can arbitrarily divide the possible program steps and does not need to input into the microcomputer beforehand the data or information that he wishes to program. Instead, the operational program is more pre-programmable through the possible choices between several data fields.

There are different programs which are possible. For example, a program with a fixed cycle plan can be utilized; however, daily changes of the cycle plan are also programmable, e.g., if during the night or other rest time pause periods are necessary. Thereby, one can also engage several changes of the program daily to provide for rest time, for example, during early afternoon.

This device for the administration or delivery of liquid medicine accommodates the daily needs of the patient very exactly. This allows a much more exact therapy than was previously possible.

In the event that at a predetermined time a completely different program should begin, the data and time for the start of the program can be given over a further data field. Several time points can be given for complete changes of the program. The microcomputer stores the program steps in memory storage locations. For example, about 300 storage locations, which can be arbitrarily divided or grouped into program fields, might be available.

It is also possible to program a manual override function which can be called upon as required by the doctor or the patient. The manual override allows the possibility of administering an additional dose of medicine by pressing a button. A manual override function is necessary for an increased need of medicine not anticipated by the program, for example, for particular physical stress or the like. There is a minimum pause time between two adjacent manual override-generated doses.

With the computer control device, it is also possible to adjust the delivery volume of each pump cycle. This makes it possible to deliver a measured volume of liquid. The user activates a key to begin and to end the delivery period. The microcomputer independently calculates the necessary speed of the motor for a desired delivery volume of the pump per minute. This possibility is important for certain medicines which are administered in very small amounts, e.g., minimal fractionary amounts.

BRIEF DESCRIPTION OF THE DRAWING

In the drawing, an embodiment of the computer-driven device for the application of liquid medicine is shown in accordance with the invention, and in fact shows:

FIG. 2 a perpendicular, longitudinal cross-section of the device;

FIG. 3 a view of the device in FIG. 1 seen from the right, whereby the top lid of the housing is removed.

DETAILED DESCRIPTION OF THE PREFERRED EMBODIMENT

Figure 1:
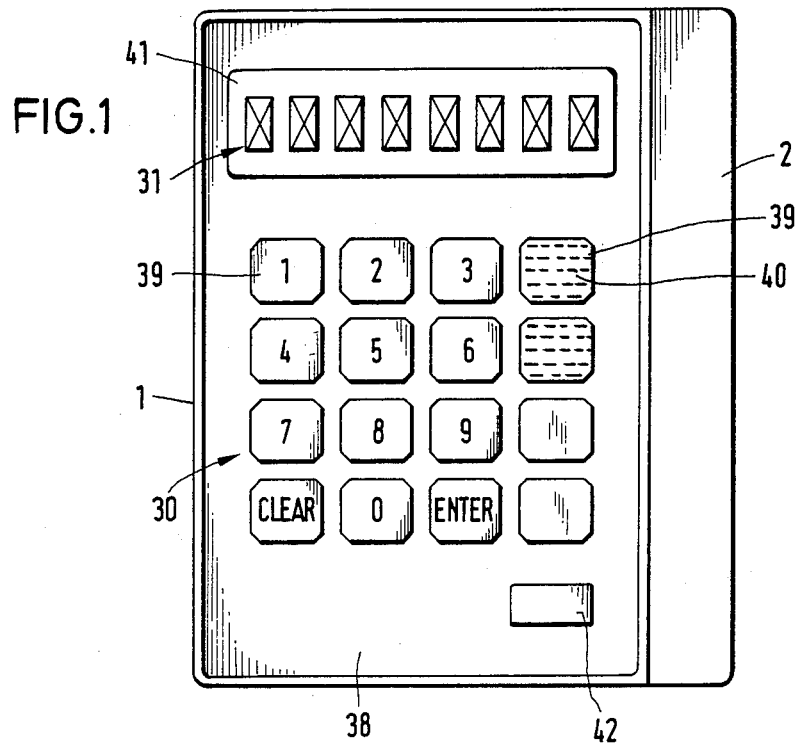
In FIG. 1 a view of the front of the device.

The embodiment shown has a boxlike housing 1 with a removable snap-on lid 2 so that the important members of the device can be approached as necessary from outside the housing. In the housing 1, there is a roller type pulsatory or rolling pump 4 connected to a drive motor 5, which is driven according to a preset program by means of an electronic control 6 and a 9-volt drive battery 7. The drive battery 7 in housing 1 is replaceable. A further battery, namely a 3-volt button cell 8, serves as a program and data safety device (i.e., to assure continuity and the preservation of the selected program and data) for the electronic control 6, when the drive battery 7 is worn out and also when the drive battery 7 is replaced. The button cell 8 in housing 1 is also replaceable.

A head 10 is rotatably connected to the drive shaft 9 of the motor 5 of the rolling pump 4. The head 10 is provided with a needle roller 11 parallel to the axis of the drive shaft 9. The needle roller 11 extends between a fixed disc 12 and a thin covering disc 13, so that it lies in a sort of guide slit 14 of the head 10.

In an opening 15 in the housing there is a large ready-made, flexible storage container 16 of about the same volume. The container 16 is for liquid medicine, specifically injection solution. The storage container 16 is connected to outlet tube 17, which is guided through the slits 14 of the head 10 of the rolling pump 4 and is thereby stretched over the needle roller 11. This tube 17 ends in a connecting piece 18 on which a catheter can be interchangeably connected. In order to tightly stretch the tube 17 on the head 10 of the rolling pump 4, sleeves 20 and 21 are connected on it, which are positioned behind a high standing wall 23 provided in the housing 1. The wall 23 contains side slits 24 for the entrance and exit of the tube 17.

The motor 5 of the rolling pump 4 is operated by direct current from the drive battery 7 respectively controlled by one of the programs determined by the electronic control 6. By inputting a digit combination, the motor 5 can be switched on independently from the previously inserted program. With a different digital combination, one can provide a manual override function independently from the control program 6.

Figure 4:
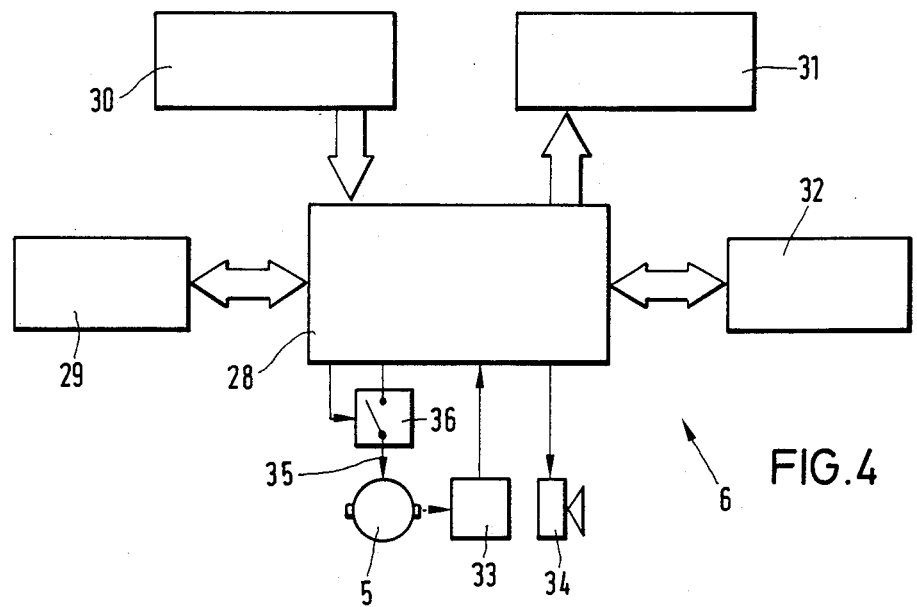
FIG. 4 a block diagram of the electronic control of the device of FIGS. 1 to 3.

The electronic control 6, which is formed as a disc-shaped plastic block 37, has a microcomputer 28 having program storage 29 as a main control element. This is shown in FIG. 4. The programming is provided by means of a keyboard 30 located in a flexible plate 38 glued to the side of the plastic block 37. The keyboard 30 has a total of sixteen keys 39 integrated in the plate 38. On the back side of the keys 39 are conductors 40 in the form of stripes which serve as contacts to the electronic control 6. Data can be entered in the program storage 29 of the microcomputer 28 by pushing the individual keys 39. An indicator 31 is located behind a viewing aperture 41 in the plate 38, as part of the electronic control 6. The display 31 is shown here in block 37 as a cast-in liquid crystal indicator panel. Behind a further viewing aperture 41 of plate 38 is the serial number of the apparatus on block 37.

The microcomputer 28 constantly compares the data of the program storage 29 with the time and date from a calendar clock 32, which is a quartz clock.

The motor 5 of the rolling pump 4 is connected to the microcomputer 28. The motor 5 is controlled in accordance with the program given by the microcomputer 28. The speed of the motor 5 is signalled by the tachometer 33 inputted to the microcomputer 28, and, if necessary, corrected. A generator 34 sounds an acoustic signal when the battery 7 must be changed, when the motor 5 operates contrary to the program or its speed is incorrect, and when a predetermined quantity of liquid injection fluid is necessary. When the signal 34 sounds, the reason therefor can be read on the display 31.

The button cell 8 provided as a safety device assures the continuity and preservation of the inputted program during replacement of the drive battery 7. The button cell also assures that the calendar clock 32 runs without interruption. The microcomputer 28 picks up the current program after the changing of the battery 7. Thus, the battery 7 can be changed during use. The battery 7 can even be changed by the patient.

The electronic control 6 (particularly the electronic elements) is encapsulated, as are the batteries 7 and 8. Thus, neither the medicinal solution from a leaky storage container 16 nor water from outside can contact voltage conducting parts.

A standard program cycle comprises a pause time (i.e., 89 minutes), a running time (i.e., 1 minute), and a pump volume (i.e., 50 microliters per minute). In order to program the device, the programmer, for example the doctor, enters a code by using the keyboard 30, whereby the microcomputer 28 is directed to be ready for programming. Various program fields can be chosen or addressed by means of the keys of the keyboard 30. The display 31 shows the data as it is entered in the relevant program field.

For example, by choice of the data field "50" on the display 31, the indicated pause time shows. This time can be re-entered with hours, minutes, and second, and so stored. By the field "51" the running time of the rolling pump 4, and subsequently the delivery time, is programmable in a similar manner. By means of the data field "52" one can program the pump volume per minute for the respective delivery times or running times.

The cycle plan repeats without further programming. In the event that a deviation from this cycle scheme is desired, e.g., when other pause times are necessary, as during the night or during rest times, one can program corresponding data over a further data field "53". The time when the deviation from the cycle plan should result is entered in field "53". By means of the fields "50" to "52" the changes can be programmed. Thereby, it is possible to provide several daily changes or deviations from the cycle plan.

In the event that a completely different program is to be run starting at a determined time point, the date and time can be entered by means of a further field "54". In the previously described manner, the daily operation of the program can be newly determined. Also in this case, there can be several time points stored for complete program changes. The program data are entered in the program storage 29 by the microcomputer 28 and stored there. For example, 300 memory locations are available which can be arbitrarily filled by data from each field "50" to "54".

The field "50" is entered by pressing one after the other of the keys "5" and "0" respectively. The corresponding procedure is followed for the other fields.

FIG. 4 further shows that a safety device 36 is built in the circuit 35 of the motor 5. This electronic safety device is on a cycle where it is normaly open for a period of time and then switches on for a period of time. The microcomputer 28 is connected with and controls the operation of the safety device 36. When the safety device 36 is switched on by the microcomputer 28, it automatically switches itself off after 0.1 seconds unless another enable signal from the microcomputer 28 is received. During normal operation of the device, the safety device is enabled by the microcomputer 28 at regular time intervals.

In the event that a member of the electronics is defective, for example, the clock, the calendar, or even the microcomputer itself, it could be possible that no signal (by element 34) is given, so that the pump system will run uncontrolled. In such a case, the electronic safety device 36 immediately opens (due to the lack of an enable signal from microcomputer 28) to switch off the motor 5 of the rolling pump 4 before harm can arise.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of the circuit and the combination and arrangement of circuit elements may be resorted to without departing from the spirit and the scope of the invention as hereinafter claimed.

What is claimed is:

1. A self-contained programmable device for the intermittent pulsatory application of liquid pharmaceuticals with a changeable storage container for the pharmaceutical wherein the storage container is connected to a catheter by a flexible tube operably associated with a motor-driven roller pump comprising electronic means for controlling operation of the pump including delivery and pause times, said electronic control means having a plurality of control functions and including a microcomputer with program storage means for storing program instructions and pump operating data, keyboard means for inputting and changing said pump operating data in said program storage means, and clock means for providing time and date information to said microcomputer, said electronic control means determining and controlling a cycle plan of the roller pump based on said program instruction, pump operating data and clock means information, said program storage means including program data fields individually addressable by operation of said keyboard means for inputting corresponding pump operating data and program changes, at least one of said data fields including programmable means to permit preprogrammed initiation of a new cycle plan at a predetermined time based on said clock means information, at least one other of said data fields including programmable means to permit preprogrammed temporary deviation in one of said cycle plans at a recurring time interval in the cycle plan based on said clock means information, followed by return to the cycle plan, said first-mentioned cycle plan including any preprogrammed deviation repeating until said predetermined time, said microcomputer constantly comparing data in said program storage means with said time and date information provided by said clock means to detect said predetermined time and begin said new cycle plan including any preprogrammed deviation, a tachometer connected to said microcomputer and operatively connected to said drive motor for monitoring the motor speed and operation of said roller pump to determine any errors.

2. A device in accordance with claim 1, further characterized in that said microcomputer includes means for detecting disturbances in the proper operation of said roller pump as monitored by said tachometer and the sufficiency of pharmaceutical supply in said storage container, and said electronic control means further includes indicator means operatively connected to the microcomputer for displaying program data field selections, entered data and disturbances.

3. A device in accordance with claim 2, further characterized in that a signal generator to indicate disturbances is connected to the microcomputer, said microcomputer energizing said signal generator when a disturbance is detected by said microcomputer.

4. A device in accordance with claim 3, further characterized in that said signal generator includes means for generating an acoustic signal.

5. A device in accordance with claim 1, further characterized in that it includes as an energy source operatively connected to said electronic control means a 9-volt block battery and a 3-volt button cell to protect stored data in said program storage means during a battery change.

6. A device in accordance with claim 1, further characterized in that in an emergency a safety device which is connected to the drive motor for the rolling pump prevent operation thereof.

7. A device in accordance with claim 6, further characterized in that said safety device completes a circuit in the drive motor, said safety device being an electronic safety device connected to the microcomputer, said safety device automatically switching off at regular intervals absent the microcomputer switching said safety device on at regular intervals.

8. A device in accordance with claim 1, wherein each control function of said electronic control means is determined by data in a corresponding one of said program data fields and can be adjusted by programming changes inputted via said keyboard means.

9. A device in accordance with claim 8, wherein one of said data field is includes programmable means to provide manual override control of the pump independently of said stored cycle plan.

10. A device in accordance with claim 1, wherein a plurality of program data fields including programmable means are provided for adjusting pump pause time, pump running time and pump volume to permit said preprogrammed temporary deviations in said cycle plans.

* * * * *